United States Patent [19]

Sanders et al.

[11] 4,403,625
[45] Sep. 13, 1983

[54] DISPOSABLE BUCCAL HYGENIC DEVICE

[76] Inventors: James B. Sanders, 1510 Beverwil Dr., Los Angeles, Calif. 90035; Don Kobashigawa, 3633 W. Olive Ave., Burbank, Calif. 91505

[21] Appl. No.: 314,431

[22] Filed: Oct. 23, 1981

[51] Int. Cl.³ .............................................. A61C 15/00
[52] U.S. Cl. ........................................................ 132/91
[58] Field of Search .................................... 132/89–93

[56] References Cited

U.S. PATENT DOCUMENTS

| | | | |
|---|---|---|---|
| 1,608,212 | 11/1926 | Hochstadter | 132/92 R |
| 2,612,177 | 9/1952 | Footer | 132/93 |
| 4,040,433 | 8/1977 | Edison | 132/93 |
| 4,326,548 | 4/1982 | Wagner | 132/90 |

Primary Examiner—G. E. McNeill
Attorney, Agent, or Firm—Birch, Stewart, Kolasch and Birch

[57] ABSTRACT

An inexpensive disposable buccal hygenic device is disclosed. An elongated cylindrical wooden body of a generally circular cross-section is pointed at each of its ends and is of such a size that the body is comparable functionally to a conventional toothpick. The elongated body is divided transversely into two separable members of generally similar length. The first member has a reduced cross-section for a distance immediately adjacent to the transverse division. The second member has an internal cavity therein contiguous with the transverse division. The internal cavity is adapted to fit slidably over the reduced cross-section portion of the first member and is of a depth at least equal to the distance of reduced cross-section on the first member so that a cavity remains when the first member is inserted fully into the second member. A strand of dental floss is provided that has one end affixed to a surface of the internal cavity not engaged by the first member and has the other end affixed to the first member internal to the elongated body. Hence, when the members are joined to form the elongated body, the strand of dental floss is stored within the cavity. On the other hand, when the members are separated, the members serve as handles to assist in proper manipulation of the dental floss about a user's teeth.

20 Claims, 8 Drawing Figures

DISPOSABLE BUCCAL HYGIENIC DEVICE

BACKGROUND OF THE INVENTION

1. Field of the Invention

This invention is related generally to buccal hygenic devices and is more particularly concerned with such a device that is inexpensive, disposable and adapted to accomplish effectively the functions of both a toothpick and dental floss.

2. Prior Art

While dental research has discounted the effectiveness of using a toothpick for removing residual food particles from interproximal tooth surfaces and spaces in favor of dental floss, many people continue to cling to the use of a toothpick to remove such debris. In addition, dental floss has been shown to be helpful in massaging the surfaces of the gums and promotes healthy gums. It is possible that the public's reluctance to accept fully the use of dental floss results partially from the present inability for merchants to provide floss to patrons of their establishments such as toothpicks are now distributed.

Previously, many devices have been offered that combined the functions of a toothpick and dental floss. Exemplary of such devices is that shown in U.S. Pat. No. 4,194,290 to Vallhonrat. This device had an elongated member that was pointed on one end and had dental floss extending tautly between two pegs depending laterally from the middle portion of the elongated member.

A similar device is disclosed in U.S. Pat. No. 3,926,201 to Katz. However, in Katz the dental floss was strung tightly between the two tips of a U-shaped portion of the device at one end, while a point was provided on the opposite end of an elongated, molded member. Katz provided no brushing capability.

Both of the foregoing devices suffer from the drawback that the dental floss is intended to be strung tightly across the pegs to which is is attached. When tightly strung, the dental floss cannot be manipulated properly to clean the interproximal surfaces of the teeth. To floss correctly requires wrapping the floss around a large interproximal surface whereby the total area is cleaned and the adjacent area of the gum massaged concomitantly.

A second group of prior art devices also combined toothpicking and flossing capabilities. These include U.S. Pat. No. 407,362 to Mason, and U.S. Pat. No. 3,930,059 to Wells. The Mason device combined a conventional toothpick with a length of conventional dental flossing material. The dental flossing material was either wound around the outside of the toothpick or fed from an open bobbin within the toothpick. In all cases, means were provided for engaging and holding the free end of the dental floss when not in use. In the Wells arrangement, the conventional length of dental floss was periodically rigidified by thickening it through application of a wax or plastic coating so that the periodically rigidified portions could be utilized as a toothpick.

Both of the foregoing devices suffer from serious drawbacks that have limited their utility. The Mason device was intended to be reused many times. While such practice was generally accepted in the 19th century, modern hygenic techniques dictate that such devices be reused only when the capability exists to regularly sterilize the instrument. Obviously, such sterilization techniques would preclude many materials from being utilized in the Mason arrangement and would, therefore, greatly increase the cost and expense involved therewith.

The Wells device, while being a reasonable solution to the problem of providing the dual functions with hygenic control, cannot satisfy the application where the user does not wish to carry a roll of dental flossing material with him at all times. Moreover, public health and safety standards preclude the provision of a roll-type device, such as taught by Wells, in a restaurant, airplane or other public accommodation for use by a variety of patrons.

Additional dental floss holding arrangements are shown in U.S. Pat. Nos. 2,981,264 to De Felice, 3,696,821 to Adams, 3,792,706 to Keese and 3,918,466 to Peebles. None of the aforementioned dental flossing devices solved the problem of providing combined toothpicking and flossing capabilities within an inexpensive, disposable unitary device.

SUMMARY OF THE INVENTION

Accordingly, it is an object of the present invention to provide an inexpensive, disposable buccal hygenic device that combines dental flossing and picking capabilities.

Another object is to provide such a device that utilizes inexpensive materials and which may be packaged and dispensed on a unitary basis in a manner analogous to that by which toothpicks are dispensed conventionally by restaurants and other places of public accommodation.

A further object is to provide such a device in which the dental flossing material is protected from the environment until such time as the user elects to expose the dental flossing material for his use, even though the user may be using the device as a toothpick.

A still further object of the invention is to provide such a device in which means are provided for assisting the user in manipulating the dental flossing material over large interproximal tooth surfaces.

Briefly, the invention in its broadest aspect comprises an inexpensive, disposable buccal hygenic device comprising a strand of dental floss and an elongated, generally cylindrical body. The generally cylindrical body has one end thereof which is narrowed sufficiently so as to enable the body to function as a toothpick. The body of the device is generally separable into two end members and an end of the strand of dental floss material is affixed to each proximal end of those two end members. In this way, when the members are separated, the members may be utilized as handles for the proper manipulation of the dental floss about the user's teeth. Furthermore, means are provided for isolating the dental floss from the atmosphere prior to the members being separated from each other to insure hygenic conditions.

Further objects, advantages and features of the invention will be apparent in the arrangement and construction of the constituent parts in detail as set forth in the following specification taken together with the accompanying drawing.

DETAILED DESCRIPTION OF THE PREFERRED EMBODIMENT

Figure 1:
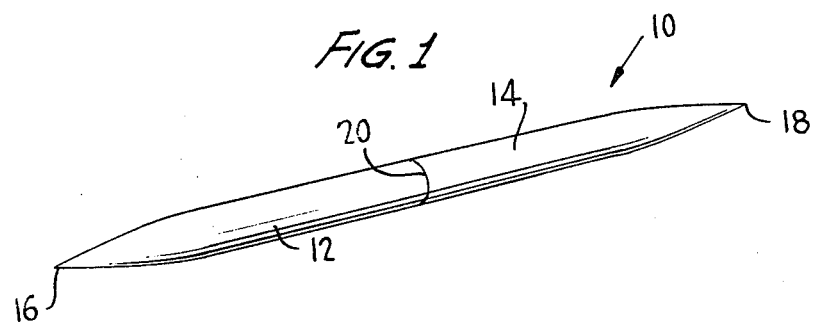
FIG. 1 is an enlarged pictoral representation of a preferred embodiment of the present invention.

In referring to the various figures of the drawing hereinbelow, like reference numerals will be utilized to refer to identical parts and features of the devices as shown therein.

Referring initially to FIG. 1, there is shown a preferred embodiment of the buccal hygenic device of the present invention indicated generally by the reference numeral 10. The device 10 is divided generally into two separable end members 12 and 14. Each of the two end members 12 and 14 has its distal end, 16 and 18, respectively, narrowed to a point such that the device 10 assumes in general size and shape the dimensions of a conventional toothpick and may be of any acceptable cross-sectional configuration, such as circular or rhombic. When in the assembled configuration shown in FIG. 1, the device 10 is capable of operating in the identical manner to a conventional toothpick.

Figure 2:
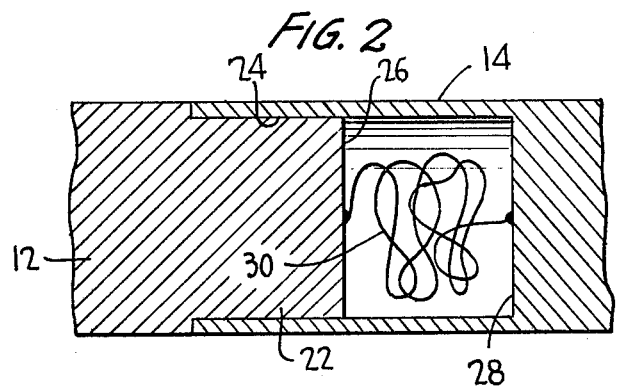
FIG. 2 is a further enlarged, partial, cross-sectional view of the preferred embodiment of FIG. 1 showing the internal constructional features of the buccal hygenic device of the present invention and demonstrating the storage repository for the dental flossing material.

The device 10 is separable at a dividing line 20. In the enlarged, cross-sectional view of the device 10 shown in FIG. 2, it may be seen that the two separable members 12 and 14 are configured so as to slidably engage at their proximal end portions. As shown in FIG. 2, member 12 has the cross-section of its center end portion 22 narrowed sufficiently to form a male plug having end surface 26 thereon. Conversely, member 14 is hollowed-out on its proximal end to provide an inner cylindrical surface 24 that slidably engages the male plug section 22. At the base of the hollowed-out portion, female member 14 has an internal end surface 28. Surfaces 26 and 28 are separated from each other in the assembled device 10 by a distance sufficient to allow a strand of dental floss 30 to be stored therein. The strand of dental floss 30 is affixed at its respective ends to surfaces 26 and 28 in any suitable manner, such as by glue.

In the foregoing fashion, when the members 12 and 14 are assembled to each other, a protected sterile compartment is formed within the device 10 for storage of the dental floss prior to its utilization. In order to assure the user that some manner of integrity exists for the compartment, it is within the purview of the invention that some manner of sealant, such as paraffin or a mild adhesive, be interposed between the surfaces 22 and 24 during assembly of the device 10. The amount utilized is that which is sufficient to maintain a seal and to be broken easily by the user.

Figure 3:
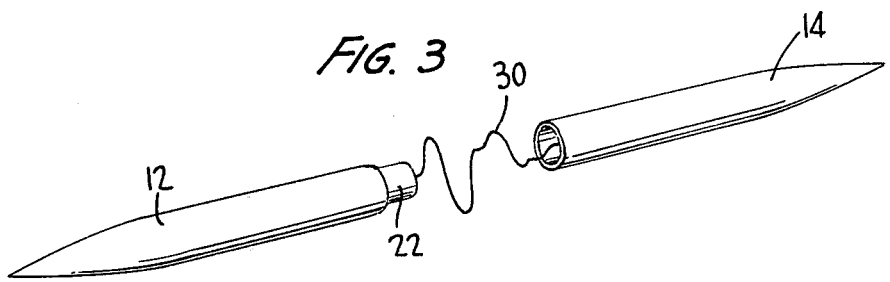
FIG. 3 is an enlarged pictoral representation of the buccal hygenic device shown in FIG. 1 where the seal has been broken to expose the dental flossing material.

Turning now to FIG. 3 of the drawing, the device is shown in its disjointed configuration with the dental floss extended between the end members 12 and 14. The length of dental floss utilized within the device 10 is that which allows the user to accomplish the proper cleaning of the interproximal surfaces of the teeth and concomitant massaging of the adjacent gum areas. Preferably, about 20 mm. of exposed length of dental floss is sufficient to permit such action to take place.

Figure 4:
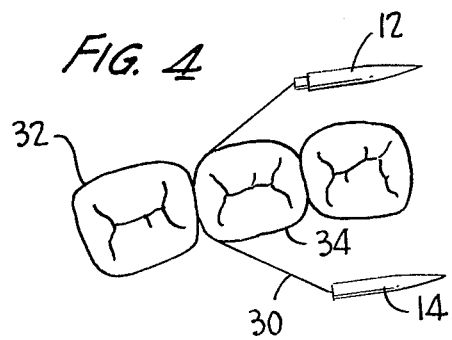
FIG. 4 is a schematic representation demonstrating the use of the device in its separated form as shown in FIG. 3 to clean large interproximal surfaces on the user's teeth.

FIG. 4 demonstrates the use of the device in cleaning the interproximal surfaces of teeth 32 and 34. As shown in FIG. 4, the freedom of orientation afforded by the device according to the invention allows the dental floss 30 to be wrapped in the proper manner about the tooth 34 during the cleaning process. Furthermore, the end members 12 and 14 in the separated configuration function as handles to assist in achieving proper manipulation, as many users find it difficult to hold the dental floss firmly when it is within the oral cavity.

Figure 5:
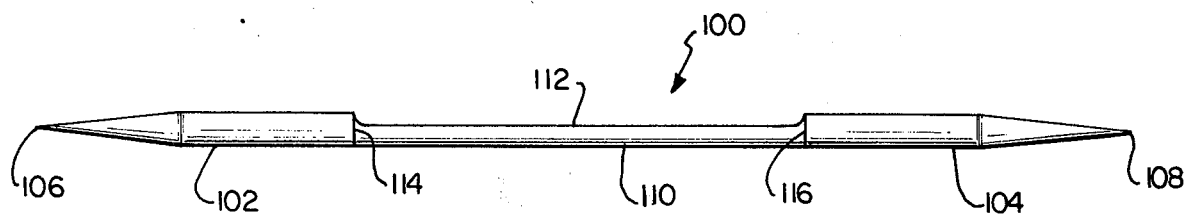
FIG. 5 is an enlarged pictoral representation of a second preferred embodiment of the present invention.
Figure 6:
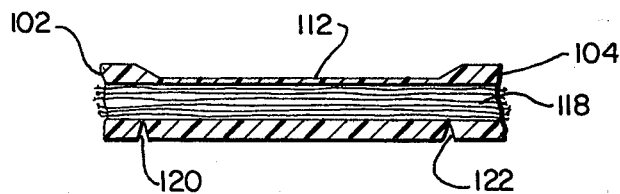
FIG. 6 is a further enlarged, partial, cross-sectional view of the preferred embodiment shown in FIG. 5.

Turning now to FIGS. 5 and 6 of the drawing, there is shown a second preferred embodiment 100 of the disposable buccal hygenic device according to the present invention. The device 100 is comprised generally of three separable sections, 102, 104 and 110. End sections 102 and 104 have respective pointed portions 106 and 108 at the distal ends thereof. The center section 110 has its cross-section reduced somewhat from that of the end sections 102 and 104 resulting in dividing lines of demarcation 114 and 116, respectively. In the preferred embodiment of the device 100, as is shown in greater detail in FIG. 6, a length of dental floss 118 is encapsulated at its ends in the end sections 102 and 104 and the usable portion stored within the center section 110. The length that is encapsulated within the center section of the device 110 may be of a single thickness or may be doubled back upon itself one or more times so as to provide a greater working length for use in the flossing process.

The device 100 shown in FIGS. 5 and 6 is preferably formed of a synthetic plastic material, such as polypropylene. In this embodiment, the reduction in cross-section area in the center section 110 is accomplished by applying only a thin, plastic, membrane-like layer 112 of the plastic material over the dental floss 118. This reduction in cross-sectional area accomplishes two purposes. First, the sharp reduction in size at 114 and 116 provides areas of stress concentration so that when the user wishes to free the dental floss, the device 100 may be broken readily at the surfaces 114 and 116 leaving the entirety of the length of dental floss 118 that was stored in the center section 110 available for use. Second, by forming only a thin membrane of plastic material over the dental floss, that layer can be rather easily ruptured longitudinally after breaking the device laterally so that the central portion can be removed completely from the dental floss material and discarded.

In some applications, it may be preferable to further score the exterior of the device 100 at the lines 114 and 116 as shown by the triangular indentations 120 and 122 in FIG. 6 to provide further areas of stress concentration to insure that the material fractures cleanly. The triangularly-shaped score marks may be filled with a material that does not bond tightly to the body 100 but which prevents the presentation of sharp edges upon which the user's mouth may be injured when the device is being utilized as a toothpick.

Figure 7:
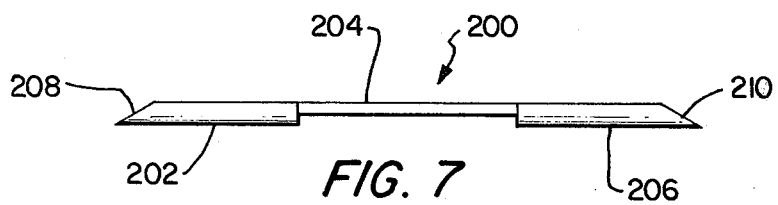
FIG. 7 is an enlarged pictoral representation of a third preferred embodiment of the present invention.
Figure 8:
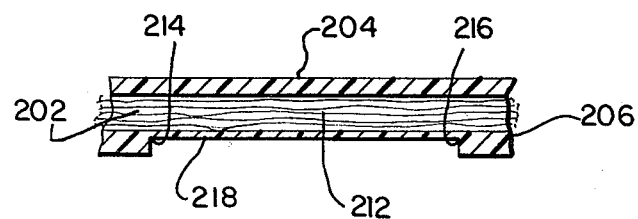
FIG. 8 is a further enlarged, partial, cross-sectional view of the third preferred embodiment of the present invention shown in FIG. 7.

FIGS. 7 and 8 show an additional preferred embodiment of the invention 200 that is similar in configuration to that shown in FIGS. 5 and 6. The device 200 consists of an end portion 202, a central portion 204 and a second end portion 206. The two end portions have pointed surfaces 208 and 210 thereon. The central section 204 is, once again, reduced in cross-sectional configuration and houses a length of dental floss 212 therein. The length of dental floss 212 is coated with a thin layer of plastic 218. Here, the outer configuration of the device 200 is restricted greatly in the central portion 204 so as to form areas of stress concentration 214 and 216 whereby the device can be readily separated into the three sections and the central section 204 thereafter discarded.

In all of the configurations shown in the drawing, the device is preferably of a size comparable to that of a conventional toothpick. In this way, the devices according to the invention may be dispensed by retail and other establishments in the manner by which conventional toothpicks are dispensed today. For example, the devices may be packaged in individual tissue paper envelopes and placed in containers adjacent to cash registers and the like. Moreover, the devices will be readily accommodated by the one-at-a-time toothpick dispensers utilized in many restaurants. Furthermore, an individual wishing to floss and otherwise care for his teeth while away from home need no longer carry a bulky dental floss dispenser with him but, on the contrary, may simply place one or more of the devices according to the present invention in a pocket or purse for later use.

While there have been shown and described what are considered to be preferred embodiments of the present invention, it will be obvious to those skilled in the art that various changes and modifications may be made therein without departing from the invention as defined in the appended claims.

What is claimed is:

1. An inexpensive, disposable buccal hygenic device comprising
    a strand of dental floss,
    an elongated, generally cylindrical body having one end thereof narrowed sufficiently to function as a toothpick, the body being generally separable into two end members, a separate end of the strand of dental floss being affixed to each proximal end of the two end members so that when the members are separated, the members may serve as handles to assist in proper manipulation of the dental floss about a user's teeth, and
    means for isolating the dental floss from the atmosphere prior to the members being separated from each other to insure hygenic conditions.

2. The device as set forth in claim 1, wherein the strand of dental floss is stored internal to the cylindrical body prior to separation.

3. The device as set forth in claim 2, wherein the elongated body is narrowed at both ends and is comparable in size to a conventional toothpick.

4. An inexpensive disposable buccal hygenic device comprising
    an elongated, generally cylindrical body having one end thereof narrowed sufficiently to function as a toothpick, the body being divided generally transversely and intermediate its ends into two separable members, one member of which has an internal cavity contiguous with the transverse division between the members, and
    a strand of dental floss, one end of which is affixed to the one member at a surface of the internal cavity, and the other end of which is affixed to the other member adjacent to the transverse division and internal to the elongated body so that when the members are joined to form the elongated body, the strand of dental floss is stored within the cavity and when the members are separated the members serve as handles for assisting in proper manipulation of the dental floss about a user's teeth.

5. The device as set forth in claim 4, wherein means is interposed between the joined members to provide a measure of sterility to the strand of dental floss housed in the internal cavity.

6. The device as set forth in claim 5, wherein the means is a circumferentially unitary layer of a sealing material.

7. The device as set forth in claim 6, wherein the sealing material is paraffin.

8. The device as set forth in claim 6, wherein the sealing material is an adhesive.

9. The device as set forth in claim 4, wherein the other member has its outer surface reduced in cross-section for a distance adjacent to the transverse division sufficiently to fit snugly within the internal cavity for the strand of dental floss.

10. The device as set forth in claim 9, wherein the elongated body has a generally circular cross-section throughout its length.

11. The device as set forth in claim 10, wherein the elongated body is pointed at both ends and is comparable in size to a conventional toothpick.

12. The device as set forth in claim 11, wherein the elongated body is formed of wood.

13. An inexpensive disposable buccal hygenic device comprising
    an elongated cylindrical wooden body of generally circular cross-section that is pointed at each of its ends and is of such size that the body is comparable functionally to a conventional toothpick,
    the elongated body being divided transversely at about the middle into two separable members, the first member having a reduced cross-section for a distance immediately adjacent to the transverse division and the second member having an internal cavity therein contiguous with the transverse division, the internal cavity being adapted to slidably fit over the reduced cross-section portion of the first member and being of a depth at least equal to the distance of reduced cross-section on the first member so that the cavity remains with the first member fully inserted into the second member, and
    a strand of dental floss, one end of which being affixed to a surface of the internal cavity not engaged by the first member and the other end of which being affixed to the first member internal to the elongated body so that when the members are joined to form the elongated body, the strand of dental floss is stored within the cavity and when the members are separated the members may serve as handles for assisting in proper manipulation of the dental floss about a user's teeth.

14. The device as set forth in claim 13, wherein the strand of dental floss has a working length of about twenty millimeters.

15. An inexpensive, disposable buccal hygenic device comprising
a strand of dental floss,
an elongated, generally cylindrical body having one end thereof narrowed sufficiently to function as a toothpick, the body being divisible longitudinally into three sections, the central section having its cross-section narrowed relative to those of the two end sections and having the strand of dental floss stored therein, the ends of the strand of dental floss are affixed to the respective ends of the end sections proximate to the central section so that the strand of dental floss is protected from exposure to the atmosphere within the body and the narrowed cross-section of the central section permitting a user to fracture readily the body within the central section to release the strand of dental floss with the end sections serving as handles to assist the user in properly manipulating the dental floss about the teeth.

16. The device as set forth in claim 15, wherein the elongated body has its exterior surface scored at the interfaces between the central and end sections to enable the user to fracture the body easily at these positions and wherein the central section includes means for facilitating stripping away of the central section to expose the strand of dental floss.

17. The device as set forth in claim 16, wherein the central section is sufficiently asymetric so that on one side through the central section the strand of dental floss is covered by a thin membrane to facilitate stripping away the central section.

18. The device as set forth in claim 17, wherein the elongated body is formed of a synthetic plastic material.

19. The device as set forth in claim 18, wherein the synthetic plastic material is a polypropylene.

20. The device as set forth in claim 16, wherein the elongated body is narrowed at both ends and is comparable in size to a conventional toothpick.

* * * * *